(12) United States Patent
Menifee

(10) Patent No.: US 12,186,227 B2
(45) Date of Patent: Jan. 7, 2025

(54) UROSTOMY BAG AND ABSORBENT INSERT SYSTEM

(71) Applicant: Julia Menifee, Las Vegas, NV (US)

(72) Inventor: Julia Menifee, Las Vegas, NV (US)

( * ) Notice: Subject to any disclaimer, the term of this patent is extended or adjusted under 35 U.S.C. 154(b) by 392 days.

(21) Appl. No.: 17/806,994

(22) Filed: Jun. 15, 2022

(65) Prior Publication Data

US 2022/0304843 A1 Sep. 29, 2022

Related U.S. Application Data

(63) Continuation-in-part of application No. 16/218,784, filed on Dec. 13, 2018, now abandoned.

(51) Int. Cl.
*A61F 5/44* (2006.01)
*A61F 5/443* (2006.01)
*A61F 5/445* (2006.01)

(52) U.S. Cl.
CPC .......... *A61F 5/4401* (2013.01); *A61F 5/4407* (2013.01); *A61F 5/445* (2013.01)

(58) Field of Classification Search
CPC ........ A61F 5/445; A61F 5/4401; A61F 5/441; A61F 5/443; A61F 5/455
See application file for complete search history.

(56) References Cited

U.S. PATENT DOCUMENTS

| 3,507,282 A | * | 4/1970 | Burding | A61F 5/445 |
| | | | | 604/333 |
| 4,224,366 A | | 9/1980 | McCabe, Jr. | |
| 4,615,923 A | | 10/1986 | Marx | |
| 5,950,285 A | * | 9/1999 | Porchia | B65D 33/259 |
| | | | | 24/585.12 |
| 6,129,716 A | * | 10/2000 | Steer | A61F 5/441 |
| | | | | 604/338 |
| 6,186,990 B1 | * | 2/2001 | Chen | A61G 9/006 |
| | | | | 604/350 |
| 6,231,553 B1 | * | 5/2001 | Hulett | A61F 5/441 |
| | | | | 604/332 |
| 6,544,241 B2 | * | 4/2003 | Morton | A61F 5/4407 |
| | | | | 604/317 |

(Continued)

FOREIGN PATENT DOCUMENTS

| WO | 2006041393 A1 | 4/2006 |
| WO | 2018187427 A1 | 10/2018 |

*Primary Examiner* — Guy K Townsend
(74) *Attorney, Agent, or Firm* — Chad G. Clark; Martensen IP

(57) ABSTRACT

Embodiments of the disclosed invention comprise a urostomy bag and an absorbent insert system, as well as methods for use. The urostomy bag comprises a storage bag having a primary aperture for interacting with a stoma on a device wearer, and a secondary aperture having a closure to seal and unseal the secondary aperture. The absorbent insert comprises a water-permeable outer layer that contains an absorbent core. The core includes a gelatinizing agent configured to make urine gelatinous. The absorbent insert is insertable into, and removable from, the inside of the storage bag via the secondary aperture. Methods for use of the disclosed urostomy system comprise attaching the urostomy bag to a wearer, inserting an unused absorbent insert into the secondary aperture, wearing the system, and replacing the used absorbent insert when required.

10 Claims, 4 Drawing Sheets

(56) References Cited

U.S. PATENT DOCUMENTS

| | | | | |
|---|---|---|---|---|
| 6,569,081 B1* | 5/2003 | Nielsen | ............... | A61F 2/0009 600/32 |
| 6,685,684 B1* | 2/2004 | Falconer | ................ | A61F 5/451 604/355 |
| 6,764,473 B2* | 7/2004 | Morton | ................ | A61F 5/4407 604/338 |
| 7,335,809 B2* | 2/2008 | Riesinger | ............ | A61F 13/0209 604/367 |
| 7,927,320 B2* | 4/2011 | Goldwasser | .......... | A61F 13/471 604/327 |
| 8,690,846 B2* | 4/2014 | Chen | .................... | A61F 13/471 4/144.1 |
| 9,655,765 B2* | 5/2017 | Timms | .................... | A61L 9/127 |
| 2003/0109838 A1* | 6/2003 | Morton | .................. | A61F 5/445 604/334 |
| 2005/0177119 A1* | 8/2005 | Tsai | ....................... | A61F 5/448 604/332 |
| 2008/0294129 A1* | 11/2008 | Giori | .................. | A61L 28/0057 428/35.2 |
| 2009/0247970 A1* | 10/2009 | Keleny | ............. | B01D 46/0036 156/247 |
| 2013/0035653 A1* | 2/2013 | Kannankeril | ........... | A61F 5/445 493/267 |
| 2014/0330229 A1* | 11/2014 | Lee | ....................... | A61F 5/441 502/62 |
| 2015/0320584 A1* | 11/2015 | Kralovec | ......... | G10K 11/17857 604/337 |
| 2020/0188162 A1* | 6/2020 | Menifee | ................ | A61F 5/4401 |
| 2020/0229962 A1* | 7/2020 | Torstensen | ............ | A61F 5/4407 |

* cited by examiner

UROSTOMY BAG AND ABSORBENT INSERT SYSTEM

CROSS-REFERENCE TO RELATED APPLICATIONS

This application is a continuation in part of U.S. application Ser. No. 16/218,784 filed Dec. 13, 2018, which is hereby incorporated by reference herein in its entirety.

BACKGROUND OF THE INVENTION

Field of the Invention

The disclosed invention includes embodiments of a urostomy bag configured to provide improved odor and leak protection.

Relevant Background

An embodiment of the disclosure meets the needs presented above by generally comprising a urostomy bag and an absorbent insert. The disclosed urostomy bag comprises a storage bag having a primary aperture for interacting with a stoma on a device wearer, and a secondary aperture having a closure to seal and unseal the secondary aperture. The absorbent insert comprises a water-permeable outer layer that contains an absorbent core. The core includes a gelatinizing agent configured to make urine gelatinous. The absorbent insert is insertable into, and removable from, the inside of the storage bag via the secondary aperture.

Existing urostomy appliances have disadvantages that the disclosed invention remedies. Chief among these is the absence of an absorbent gel insert with a deodorizing agent. Such appliances require the wearer to drain waste directly from the appliance into a toilet or other waste receptacle, which is difficult for people with mobility issues, including people using a wheelchair. Existing urostomy appliances are also rather large, usually 12 inches or more in length, which may be heavy when filled, and can interfere with clothing. For example, U.S. Pat. No. 3,507,282, filed Jan. 10, 1968 ("Burding") is a colostomy bag configured for handling solid waste that does not include a zipper closure, does not include a gelatinizing agent, and features a secondary opening located at the bottom of the ostomy bag, rather than on the perimeter and on the side of the ostomy bag as disclosed herein. Similarly, U.S. Pat. No. 6,231,553 B1, filed May 15, 2001 ("Hulett") is another colostomy appliance with a leak-prone closure on the bottom of the bag, and does not include an absorbent insert, or a gelatinizing agent. Finally, U.S. Pat. No. 7,927,320 B2 ("Goldwasser") is a disposable appliance configured to fit over the genital area to collect both solid and liquid waste, and includes neither a resealable secondary opening nor a removable absorbent insert.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

Features and objects of the disclosed invention and the manner of attaining them will become more apparent, and the invention itself will be best understood, by reference to the following description of one or more embodiments taken in conjunction with the accompanying drawings and figures imbedded in the text below and attached following this description.

The Figures imbedded and attached depict embodiments of the disclosed invention for purposes of illustration only. One skilled in the art will readily recognize from the following discussion that alternative embodiments of the structures and methods illustrated herein may be employed without departing from the principles of the invention described herein.

DEFINITIONS

Figure 1:
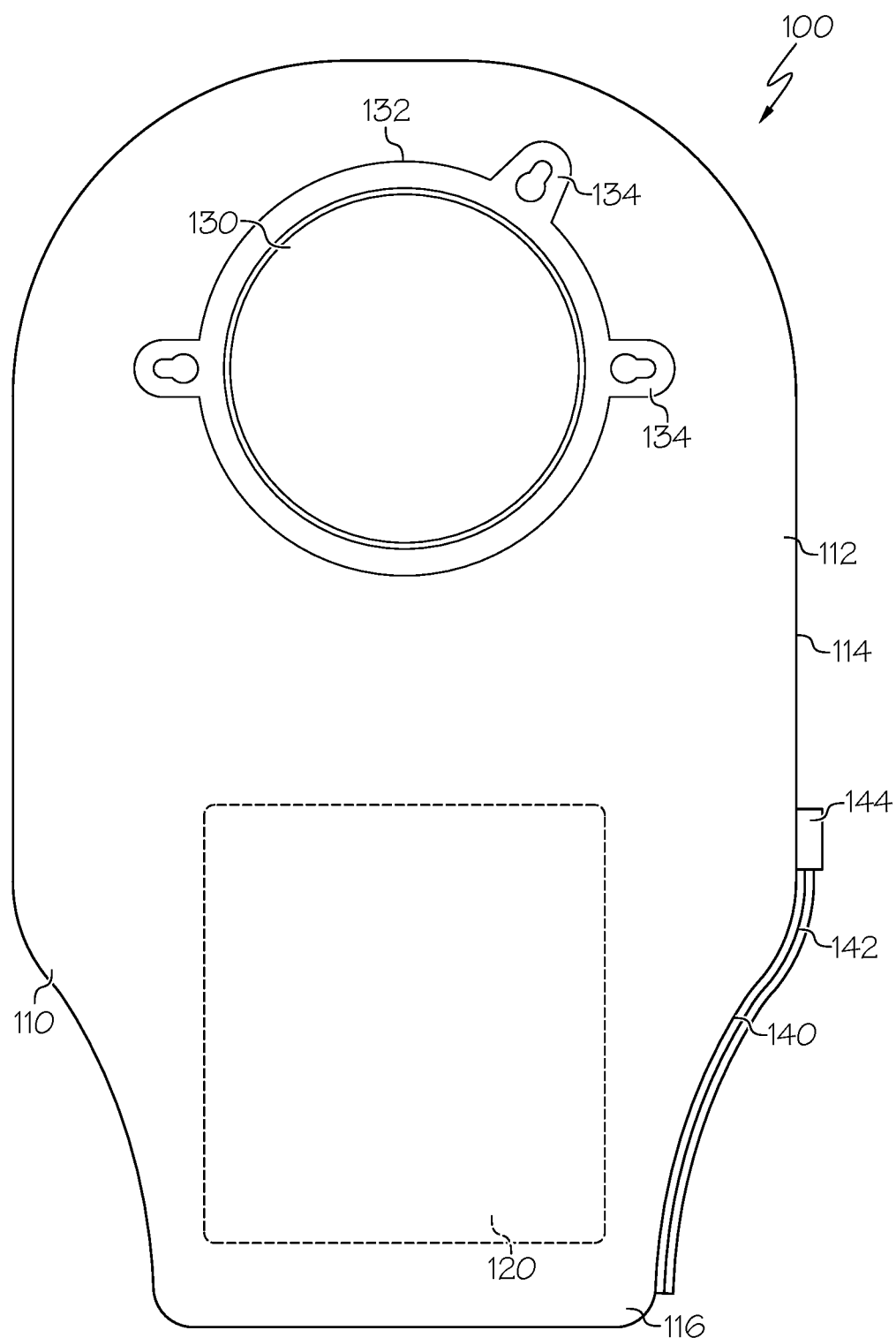
FIG. 1 is a rear view of an embodiment of the disclosed urostomy bag and absorbent insert assembly.

Urostomy means a medical procedure to create a stoma, or artificial opening, for the urinary system through the wall of the abdomen. Ostomy refers to such a procedure that may include a urostomy or colostomy procedure.

DETAILED DESCRIPTION OF THE INVENTION

What is disclosed herein are embodiments of a new device comprising an ostomy bag and absorbent insert as shown and described.

Embodiments of the disclosed invention are hereafter described in detail with reference to the accompanying FIGS. 1 through 4. Although the invention has been described and illustrated with a certain degree of particularity, it is understood that the present disclosure has been made only by way of example and that numerous changes in the combination and arrangement of parts can be resorted to by those skilled in the art without departing from the spirit and scope of the invention.

The following description with reference to the accompanying drawings is provided to assist in a comprehensive understanding of exemplary embodiments of the disclosed invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. Also, descriptions of well-known functions and constructions are omitted for clarity and conciseness.

The terms and words used in the following description and claims are not limited to the bibliographical meanings but are merely used by the inventor to enable a clear and consistent understanding of the invention. Accordingly, it should be apparent to those skilled in the art that the following description of exemplary embodiments of the disclosed invention are provided for illustration purpose only and not for the purpose of limiting the invention as defined by the appended claims and their equivalents.

By the term "substantially" it is meant that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

The terminology used herein is for the purpose of describing particular embodiments only and is not intended to be limiting of the invention. As used herein, the singular forms "a," "an," and "the" are intended to include the plural forms as well, unless the context clearly indicates otherwise. Thus, for example, reference to "a component surface" includes reference to one or more of such surfaces.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be also understood that when an element is referred to as being "on," "attached" to, "connected" to, "coupled" with, "contacting", "mounted," etc., another element, it can be directly on, attached to, connected to, coupled with, or contacting the other element or intervening elements may also be present. In contrast, when an element is referred to as being, for example, "directly on," "directly attached" to, "directly connected" to, "directly coupled" with, or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper," and the like may be used herein for ease of description to describe one element or feature's relationship to another element(s) or feature(s) as illustrated in the figures. It will be understood that the spatially relative terms are intended to encompass different orientations of a device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly," "downwardly," "vertical," "horizontal," and the like are used herein for the purpose of explanation only unless specifically indicated otherwise.

Ostomy Bag and Absorbent Insert

With reference to FIG. 1, the disclosed invention includes a urostomy system 100 comprising an ostomy bag 110 and absorbent insert 120. The ostomy bag 110 comprises a storage bag 112 having a perimeter 114, a front, and a back. The disclosed ostomy bag 110 is less than 12 inches in length from top to bottom, and preferably is 6 to 7 inches in length and 6 to 7 inches wide. The storage bag 112 is made of water-impermeable and odor-resistant polymer, and in preferred embodiments is translucent. The storage bag may be made from a polyvinyl chloride film. The storage bag 112 has a primary aperture 130 located near a top of the bag 112 and extending through the back to an inside, and a secondary aperture 140 located at or near a bottom of the bag 112 and extending through the perimeter 114 to the inside. The storage bag is permanently sealed along the perimeter 114, with the exception of the secondary aperture 140, which can be selectively sealed or unsealed by means of a closure 142. The primary aperture 130 includes a sealing ring 132 that is configured to interact mechanically with a wafer (not shown) to form a watertight seal. The sealing ring is made of a polymer, plastic, nylon, rubber, or other material. The primary aperture 130 and sealing ring 132 are sized to fit around an ostomy opening in the wearer's abdomen. The ostomy opening includes a stoma, which projects out from the wearer's abdomen. The wafer is configured to fit around the stoma and is removably attached to the wearer's skin by an adhesive to form a watertight seal. The sealing ring 132 includes a plurality of tabs 134 (three are shown) that are configured to mechanically interact with corresponding slots on the wafer to removably secure the sealing ring to the wafer, and hence the ostomy bag 110 to the wearer. The sealing ring and wafer thus create a sealed pathway for waste from the wearer's body to the inside of the storage bag.

The secondary aperture 140 is sealed and unsealed by means of a closure 142 that is mechanically attached to the storage bag 112 around the secondary opening. The closure 142 may be a zipper-type closure having a slider 144 configured to close and open the secondary aperture 140 by moving the slider alternately to a closed or to an open position. Other types of resealable closure systems are possible and contemplated, such as a hook and loop closure, a tongue and groove closure, a snap closure, or other suitable configuration. In some embodiments, the secondary aperture is located along the bottom of the storage bag (not shown). In other embodiments, the secondary aperture is located along a side of the storage bag 112. In such side-opening embodiments, the secondary aperture 140 begins just above the bottom of the storage bag 112 to create a reservoir 116 for liquid waste to collect in the sealed area below the secondary aperture.

Figure 2:
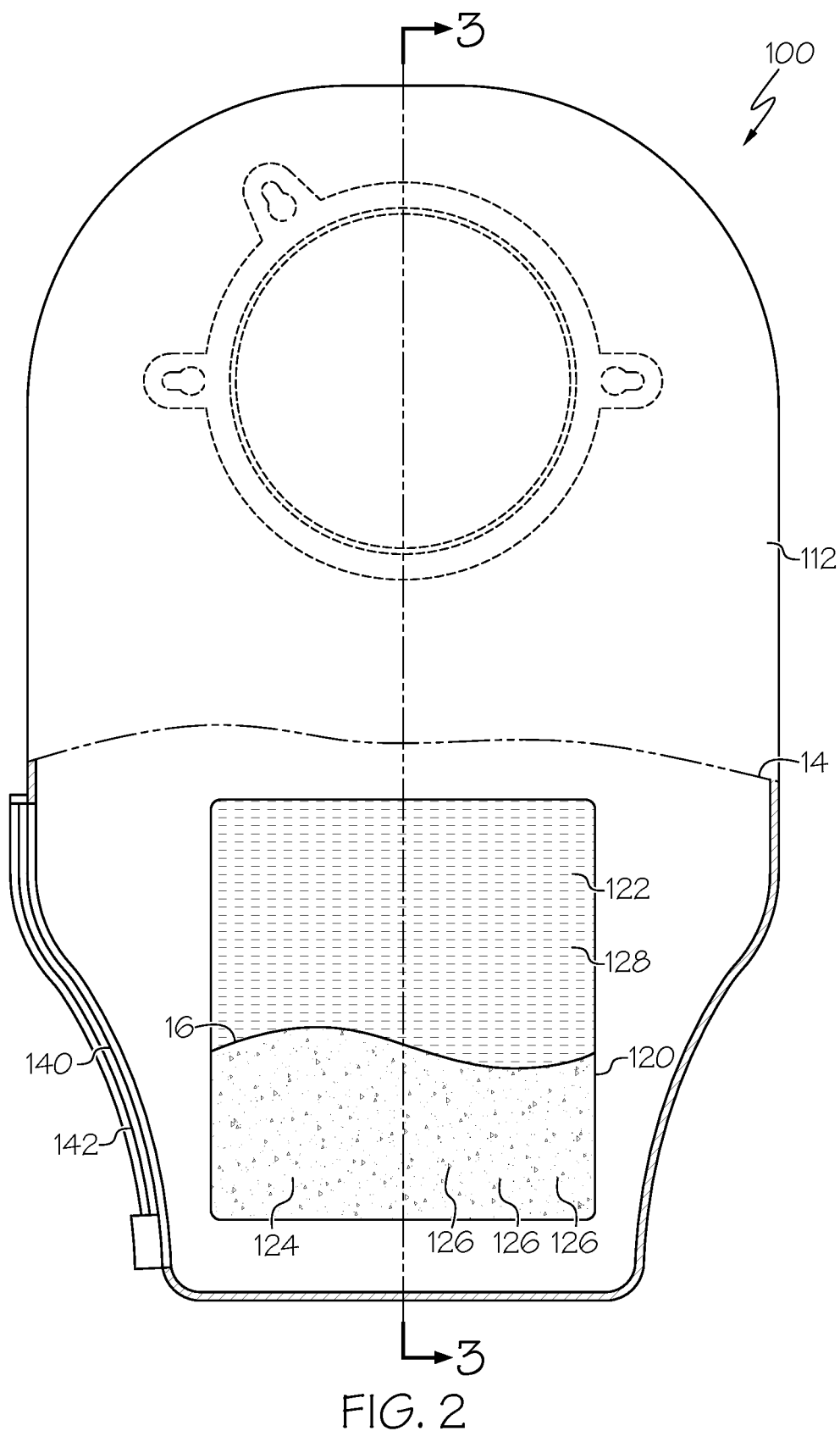
FIG. 2 is a front view of an embodiment of the disclosed invention as seen with a portion of the front panel cut away.

With reference to FIG. 2, a front view of the urostomy bag assembly 100 is shown with a lower front portion of the storage bag 112 cut away along the line 14 to allow a view of the absorbent insert 120. The absorbent insert itself is shown with a cutaway along the line 16, to allow a view of the insert's interior. The absorbent insert 120 includes, and is covered by, a water-permeable outer layer 122. The outer layer may be a nonwoven fabric made of wood fiber, polypropene, polyethylene, polyester, viscose, or other suitable material. In some embodiments, the outer layer 122 includes a deodorizer 128 coupled within its material. The deodorizer may be for example, sodium bicarbonate, diethylene glycol, activated charcoal, silica gel, or other material. The absorbent insert also includes one or more core(s) 124 that includes a gelatinizing agent 126. The one or more cores functions to provide structure to the gelatinizing agent or to contain the agent, and may be made of cellulose, nonwoven fabric, viscose, or other material. The gelatinizing agent may be a super absorbent polymer, sodium polyacrylate, potassium acrylate, alkyl acrylate, tragacanth, pectin, starch, carbomer, carrageenan, sodium alginate, gelatin, or others. The core 124 is contained within the outer layer 122, and is configured to absorb urine, capture it, and render it gelatinous. The absorbent insert 120 is insertable into, and removable from the inside of the storage bag 112 through the secondary aperture 140.

Figure 3:
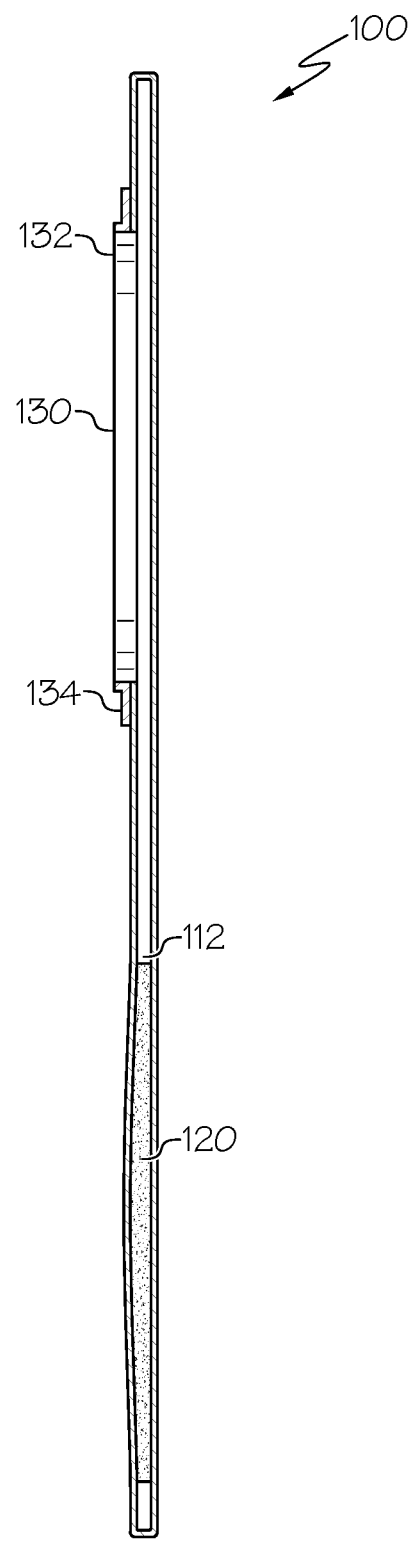
FIG. 3 is a side view of an embodiment of the disclosed invention as seen along the line 3-3 of FIG. 2.

With reference to FIG. 3, a side view of the disclosed ostomy bag assembly 100 is shown. The primary aperture 130 is shown extending through the back of the storage bag 112 to the inside of the bag. The sealing ring 132 is mechanically attached to the storage bag material around the primary aperture 130 to form a watertight seal with the storage bag 112. The sealing ring may be attached to the storage bag by use of an adhesive, ultrasonic welding, melting, or other suitable technique. In some embodiments, the sealing ring 132 includes a lip 134 that has a larger diameter than the primary aperture to facilitate a secure, fluid-tight attachment between the sealing ring and the storage bag around the primary aperture.

Figure 4:
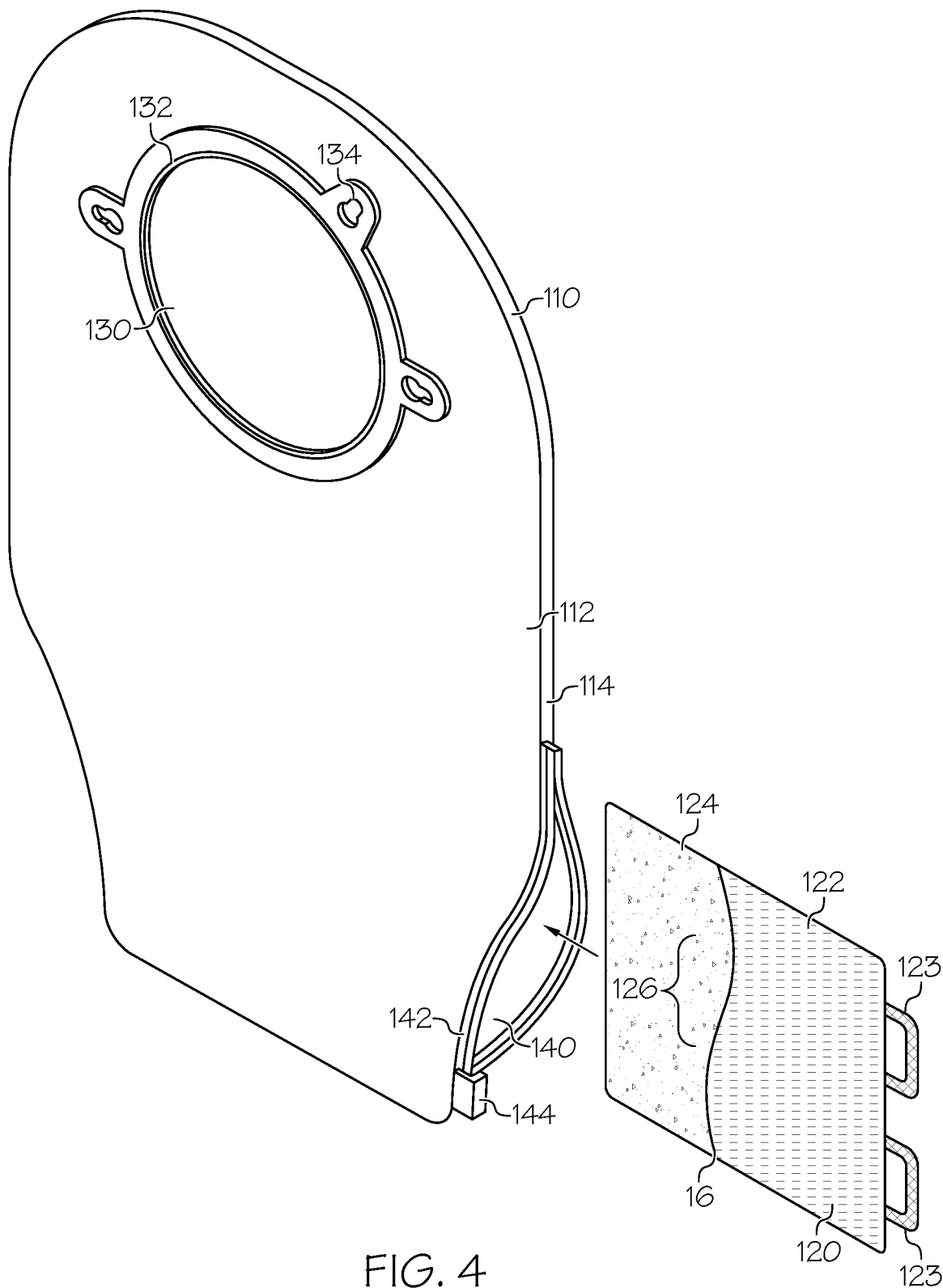
FIG. 4 is an isometric view of an embodiment of the disclosed invention.

FIG. 4 shows a perspective view of the disclosed ostomy bag 110 with the absorbent insert 120 removed. The secondary aperture 140 is shown open or unsealed, with the slider 144 of the closure 142 shown in the open position. The absorbent insert 120 is depicted with the outer layer 122 cutaway along the line 16 to allow a view of the core 124 that includes the gelatinizing agent 126. In some embodiments, one or more handles 123 (two are shown) are attached to the outer layer 122 to aid insertion and removal of the absorbent insert.

The ostomy bag 110 is prepared for use by opening the secondary aperture 140 and placing an unused absorbent insert 120 inside the storage bag 112, and closing or resealing the secondary aperture. The ostomy system 100 is then removably attached to a wearer by placing the primary aperture 130 over the wearer's ostomy opening, aligning the sealing ring 132 with the wafer, and snapping the sealing ring 132 into place on the wafer. When the wearer urinates, urine enters the storage bag 112 through the primary aperture where it contacts the absorbent insert 120. The gelatinizing agent 126 turns the urine into a gelatinous consistency and reduces contact between the urine and the primary and secondary apertures to prevent leakage. In some embodiments, the deodorizer 128 acts to neutralize or absorb odors and prevent them from leaving the storage bag 112. The ostomy bag 110 may be used for an extended period, e.g., 1-2 hours, 2-3 hours, 3-4 hours, 4-5 hours, or 5-6 hours, without being removed from the wearer's body. When necessary or desirable, a used absorbent insert 120 may be removed through the secondary aperture 140 and replaced with an unused absorbent insert.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

As will be understood by those familiar with the art, the disclosed invention may be embodied in other specific forms without departing from the spirit or essential characteristics thereof. Likewise, the particular naming and division of the modules, managers, functions, systems, layers, features, attributes, methodologies, and other aspects are not mandatory or significant, and the mechanisms that implement the invention or its features may have different names, divisions, and/or formats.

Accordingly, the disclosure of the disclosed invention is intended to be illustrative, but not limiting, of the scope of the invention.

This has been a description of the disclosed invention along with a preferred method of practicing the invention, however the scope of the inventions ought to be determined by the appended claims.

What is claimed is:

1. A urostomy bag and absorbent insert system, comprising:
   a urostomy bag, comprising:
      a storage bag, having a top, a bottom, a perimeter, a front, and a back, wherein the front and the back are sealed together along the perimeter, top, and bottom;
      a primary aperture extending through the back to an inside of the storage bag, the primary aperture configured to collect urine from a wearer;
      a secondary aperture located in the perimeter, the secondary aperture extending through the perimeter to the inside, the secondary aperture having a first end nearer to the top and a second end nearer to the bottom;
      a reservoir configured to hold liquid waste, wherein the reservoir is located at the bottom of the storage bag; and
      a closure coupled to the storage bag, the closure sealing and alternatively unsealing the secondary aperture; and
   an absorbent insert, comprising:
      an outer layer, the outer layer being permeable; and
      one or more cores located within the outer layer, the core(s) containing a gelatinizing agent, wherein the absorbent insert is insertable into, and removable from, the urostomy bag via the secondary aperture.

2. The urostomy bag and absorbent insert system of claim 1, the absorbent insert further comprising a deodorizer incorporated within the outer layer.

3. The urostomy bag and absorbent insert system of claim 1, wherein the closure is a zipper, and wherein the zipper seals the secondary aperture when positioned at a closed position and the zipper unseals the secondary aperture when positioned at an open position.

4. The urostomy bag and absorbent insert system of claim 1, wherein the absorbent insert includes one or more handles attached to the outer layer.

5. A urostomy bag and absorbent insert system, comprising:
   a urostomy bag, comprising:
      a storage bag having a front, a back, a top, a bottom, a perimeter, a primary aperture extending through the back to an inside, and a secondary aperture extending through the perimeter to the inside, wherein the front and the back are permanently sealed along the bottom; and a closure coupled to the storage bag, the closure sealing and alternatively unsealing the secondary aperture;

an absorbent insert, comprising:

an outer layer;

one or more core(s);

a gelatinizing agent coupled within the core(s); and a deodorizer incorporated within the outer layer;

wherein the outer layer is permeable and contains the core; and wherein the absorbent insert is insertable into, and removable from, the urostomy bag via the secondary aperture.

6. The urostomy bag and absorbent insert system of claim 5, wherein the closure is a zipper, wherein the secondary aperture has a first end located nearer to the top and a second end located nearer to the bottom, and wherein the second end is located a distance from the bottom.

7. The urostomy bag and absorbent insert system of claim 5, wherein the absorbent insert includes one or more handles attached to the outer layer.

8. A method of using the system of claim 1, the method comprising:

snapping a sealing ring in place to form a seal between a urostomy appliance and an appliance wearer's skin;

opening a secondary aperture in a storage bag of the urostomy appliance using of a closure;

inserting a first absorbent insert through the secondary aperture to an inside of the storage bag;

resealing the secondary aperture using the closure;

using the system for a period of time;

opening the secondary aperture using the closure;

removing the first absorbent insert through the secondary aperture;

inserting a second absorbent insert through the secondary aperture to the inside; and resealing the secondary aperture using the closure.

9. The method of claim 8, wherein the period of time is one of the following: 1 to 2 hours, 2 to 3 hours, 3 to 4 hours, 4 to 5 hours, or 5 to 6 hours.

10. The method of claim 8, wherein the closure is a zipper closure.

* * * * *